United States Patent
Smith et al.

(10) Patent No.: US 7,568,381 B2
(45) Date of Patent: Aug. 4, 2009

(54) APPARATUS AND METHOD FOR SURFACE PROPERTY MEASUREMENT WITH IN-PROCESS COMPENSATION FOR INSTRUMENT FRAME DISTORTION

(75) Inventors: Stuart T. Smith, Charlotte, NC (US); Jonathan D. Ellis, Stevensville, MD (US)

(73) Assignee: University of North Carolina at Charlotte, Charlotte, NC (US)

( * ) Notice: Subject to any disclaimer, the term of this patent is extended or adjusted under 35 U.S.C. 154(b) by 0 days.

(21) Appl. No.: 11/780,208

(22) Filed: Jul. 19, 2007

(65) Prior Publication Data
US 2008/0028840 A1    Feb. 7, 2008

Related U.S. Application Data

(60) Provisional application No. 60/834,846, filed on Aug. 2, 2006.

(51) Int. Cl.
*G01N 3/48* (2006.01)
(52) U.S. Cl. .......................................................... 73/81
(58) Field of Classification Search ............... 73/81, 73/78, 82, 83, 85, 104, 105
See application file for complete search history.

(56) References Cited

U.S. PATENT DOCUMENTS

| | | | |
|---|---|---|---|
| 5,955,661 A * | 9/1999 | Samsavar et al. | 73/105 |
| 6,691,564 B2 * | 2/2004 | Anderberg | 73/81 |
| 6,734,425 B2 * | 5/2004 | Hantschel et al. | 250/306 |
| 7,091,476 B2 * | 8/2006 | Kley | 250/234 |
| 2001/0000279 A1 * | 4/2001 | Daniels et al. | 73/105 |
| 2004/0051542 A1 * | 3/2004 | Miles et al. | 324/754 |
| 2005/0005688 A1 * | 1/2005 | Samsavar et al. | 73/105 |
| 2005/0050947 A1 * | 3/2005 | Kitajima et al. | 73/105 |
| 2005/0066714 A1 * | 3/2005 | Adderton et al. | 73/105 |

* cited by examiner

*Primary Examiner*—Hezron Williams
*Assistant Examiner*—Gunnar J Gissel
(74) *Attorney, Agent, or Firm*—Clements Bernard PLLC; Christopher L. Bernard

(57) ABSTRACT

The present invention provides an apparatus and method for performing surface property measurements, such as workpiece hardness and other material property measurements, with in-process compensation for instrument frame distortion and the like. The apparatus includes a substantially rigid base; a stylus coupled to the substantially rigid base, the stylus configured and selectively positioned to interact with a surface of a specimen at points along a central axis of the stylus; a proximity detector sensor coupled to the substantially rigid base, the proximity detector sensor disposed at a predetermined distance from the surface of the specimen and operable for sensing the predetermined distance between the proximity detector sensor and the surface of the specimen; and a proximity detector actuator coupled to the substantially rigid base, the proximity detector actuator operable for maintaining the predetermined distance between the proximity detector sensor and the surface of the specimen as the substantially rigid base and the stylus are moved with respect to the surface of the specimen along the central axis of the stylus.

24 Claims, 4 Drawing Sheets

APPARATUS AND METHOD FOR SURFACE PROPERTY MEASUREMENT WITH IN-PROCESS COMPENSATION FOR INSTRUMENT FRAME DISTORTION

CROSS-REFERENCE TO RELATED APPLICATION(S)

The present non-provisional patent application claims the benefit of priority of U.S. Provisional Patent Application No. 60/834,846 (Stuart T. SMITH et al.), filed on Aug. 2, 2006, and entitled "Method and Apparatus for Measuring Surface Properties Without Instrument Frame Stiffness Dependency," the contents of which are incorporated in-full by reference herein.

FIELD OF THE INVENTION

The present invention relates generally to the precision metrology field. More specifically, the present invention relates to an apparatus and method for performing surface property measurements, such as workpiece hardness and other material property measurements, with in-process compensation for instrument frame distortion and the like.

BACKGROUND OF THE INVENTION

In general, instruments for performing surface property measurements on specimens, typically referred to as "indentation" tests, are commonly used in many laboratories. Specifically, workpiece hardness (defined as the force required to deform an area, H=F/A) is used to characterize a specimen's resistance to both plastic and, in some cases, elastic deformation. Workpiece hardness is one of the key parameters for determining the mechanical/tribological characteristics of a workpiece and once workpiece hardness is determined, other material properties, such as modulus and yield strength, are easier to characterize. Specimens are measured to ascertain their present hardness values, and the related manufacturing processes are adjusted to adhere to specification requirements. In other words, hardness values are often used to maintain the quality of parts produced via manufacturing processes. The characterization of material properties on the nanoscale is critical in the thin films industry, for example (i.e. with respect to tool coatings, adhesives, micro-electro-mechanical systems (MEMS) semiconductors, chemo-mechanical polishing, etc.). The forces applied are typically less than about 40 mN and the indentation depths induced are typically less than about 200 nm (i.e. nanoscale surface property measurements are typically non-destructive).

In order to adhere to increasingly tight specification requirements, accurate, reliable, and traceable surface property measurements are required. A major contributor to uncertainties in these surface property measurements is instrument frame and stage distortion. Some contributors to instrument frame and stage distortion are static and dynamic loading, thermal effects, material stability, and mechanical hysteresis. Most of these influences are neither linear, repeatable, nor reversible, and are thus difficult to deconvolve.

In order to account for the above-referenced influences, conventional instruments for performing surface property measurements have attempted to characterize, predict, and compensate for instrument frame and stage distortion. Specifically, this has been done under load, using an amorphous material of known hardness to characterize the stiffness of the instrument frame and stage. Deviations from a known measurement have been deemed representative of instrumental effects. This is a particularly important procedure for calibrating micro and nano instruments that depend on the simultaneous and coincident measurement of forces and relative motions transmitted around the instruments. Unfortunately, the result is often corrected measurements that are not independent of scale, resulting in large uncertainties for measurements that differ significantly from those experienced during the characterization process. Thus, conventional characterization processes do not adequately detect or compensate for non-linear, non-repeatable, or time-dependent influences.

In addition to resulting in size-dependent measurements, calibration using an amorphous material (i.e. the specimen itself) inherently changes the stiffness of the instrument frame and stage, adding further uncertainty to the calibration process. The stiffness of the amorphous material is typically different from the stiffness of the specimen, for example.

In order to measure the depth of penetration of a stylus into the surface of a specimen, conventional instruments for performing surface property measurements use a combination of distortion calibration and the calculation of the displacement of the related force sensor (also referred to as the "load cell") used to measure the applied load. In addition to the above-referenced uncertainties associated with the distortion calibration, there are additional uncertainties in deconvolving which displacements in the force sensor are related to distortions and which are related to the depth of penetration of the stylus into the surface of the specimen.

Thus, what are still needed in the art are apparatuses and methods that remove many of the above-referenced uncertainties and minimize the significance of those that remain. Preferably, those uncertainties that remain are of a variety that may be predicted, estimated, and/or compensated for with a relatively high degree of certainty.

BRIEF SUMMARY OF THE INVENTION

The present invention provides an apparatus and method for performing surface property measurements that are determined via the relationships between the geometries of styli and the relative penetration geometries into a specimen under known loading conditions. These measurements typically depend heavily on the characterization of the stiffness and stability of the instrument frame and stage. The methodology of the present invention significantly reduces the dependency on instrument frame and stage characterization. This is achieved by measuring, via a reference sensor, the relative location of a stylus and the surface of a workpiece as forces are applied. Using such an instrument, property values such as rate-dependent hardness, elastic modulus, scratch resistance, and plastic-elastic behavior may be determined with known uncertainties. Known and constant relative proximity between the reference sensor and the surface of the specimen effectively removes from the measurement process the effects of deflections in the instrument frame and stage.

The present invention enables accurate surface property measurements, such as rate-dependent hardness, elastic modulus, scratch resistance, and plastic-elastic behavior via in-process compensation for instrument frame and stage distortions. Coincidences between the structural components of the surface property measurement instrument (i.e. metrology loops) and the structural components through which forces are transmitted (i.e. force loops) are minimized, being present only in the stylus applying a force and a mount for the stylus and force sensor, which is inherently unavoidable for any surface property measurement instrument that measures distortions in the region of applied forces.

In general, the surface property measurement instrument of the present invention includes a force sensor or load cell to which a base is attached. An indenter base is attached to this base, to which a stylus is attached. Optionally, the central axis of the stylus is normal to the surface of a specimen. The term "stylus" refers to a "tip" that is mechanically contacted with the specimen. One of the primary goals of the surface property measurement instrument is to measure the forces and resulting distortions that result from this contact. Hereinafter, this "tip" is referred to as an "indenter stylus." The force sensor or load cell is typically sensitive in directions both collinear with and normal to the central axis of the indenter stylus, such that the force interaction between the indenter stylus and the specimen may be measured. The load cell includes a sensor, hereinafter referred to as the "load cell position sensor," and compliant supports, hereinafter referred to as the "load cell supports," whereby changes in the load cell position sensor may be correlated to a force in the load cell via the known stiffnesses of the load cell supports. A base actuator is employed to translate the load cell and indenter stylus assembly with respect to the surface of the specimen, typically in a direction either towards/away from (for indenting) or along (for scratching) the surface of the specimen. The base is supported with respect to the base actuator by the load cell supports, which include one or more of the following: a mechanical connection, a hydrostatic connection, an aerostatic connection, an electrostatic connection, and/or a magnetic connection. The actuator controlling the motion of the device is mounted on a platform, on which other components are also mounted.

Preferably, the surface property measurement instrument includes an actuator that moves a proximity sensor, described in greater detail herein below, relative to the base. Hereinafter, this is referred to as the "proximity sensor actuator." One sensor is hereinafter referred to as the "proximity detector sensor" and is attached to the base via the proximity sensor actuator. This proximity detector sensor is used to determine the relative proximity between a proximity detector "tip" and the surface of the specimen. Once a desired proximity is achieved, the proximity detector sensor value is held constant under closed loop control, whereby the proximity sensor actuator maintains the proximity detector sensor value as indents or scratches are induced using the base actuator and indenter stylus. In general, this closed loop control is achieved by continuously driving the proximity sensor actuator until the error between the desired proximity detector sensor value and the desired proximity is zero. Another sensor measures the relative position between the proximity detector sensor and the base.

In general, the displacement of the load cell position sensor in a direction normal to the surface of the specimen during a contact cycle includes the penetration of the indenter stylus into the surface of the specimen, the distortion of the instrument frame and base during measurement, and the distortion of the load cell during measurement. Related to the present invention, the penetration of the indenter stylus into the surface of the specimen is the displacement measured by the proximity detector sensor while the indenter stylus is in contact with the surface of the specimen. Thus, distortions in the instrument frame and stage may be directly measured and are the difference between the displacement of the load cell position sensor and the displacement of the proximity sensor actuator during measurement.

In order to increase the operability of the surface property measurement instrument, positioning systems on which the specimen is mounted are considered. These positioning systems are typically feedback-based, whereby an operator may control the location of the test site on the surface of the specimen. This allows for indentation-scratch measurements where the applied load, depth of penetration, and/or geometry of the scratch may be of interest.

The platform that represents the present invention includes a system whereby the indentations-scratches on the surface of the specimen may be examined. This is typically a modular system with a plurality of actuators and sensors that may be interchanged in order to measure the dimensional, optical, electrical, and/or magnetic properties of the resulting indentation-scratch. A variety of well known techniques are contemplated, such as those established in the scanning probe microscopy field.

In many applications, it is desirable that the surface property measurement instrument of the present invention be housed in a chamber to monitor and control environmental conditions and effects. Temperature, pressure, and humidity sensors may be employed and used to provide feedback such that fluctuations from desired values may be minimized. All components described herein may be manufactured to be vacuum compatible, for example.

In summary, in one exemplary embodiment, the present invention provides an apparatus for performing surface property measurements, such as workpiece hardness and other material property measurements, with in-process compensation for instrument frame distortion and the like, the apparatus including: a substantially rigid base; a stylus coupled to the substantially rigid base, the stylus configured and selectively positioned to interact with a surface of a specimen at points along a central axis of the stylus; a proximity detector sensor coupled to the substantially rigid base, the proximity detector sensor disposed at a predetermined distance from the surface of the specimen and operable for sensing the predetermined distance between the proximity detector sensor and the surface of the specimen; and a proximity detector actuator coupled to the substantially rigid base, the proximity detector actuator operable for maintaining the predetermined distance between the proximity detector sensor and the surface of the specimen as the substantially rigid base and the stylus are moved with respect to the surface of the specimen along the central axis of the stylus.

In summary, in another exemplary embodiment, the present invention provides a method for performing surface property measurements, such as workpiece hardness and other material property measurements, with in-process compensation for instrument frame distortion and the like, the method including: providing a substantially rigid base; providing a stylus coupled to the substantially rigid base, the stylus configured and selectively positioned to interact with a surface of a specimen at points along a central axis of the stylus; providing a proximity detector sensor coupled to the substantially rigid base, the proximity detector sensor disposed at a predetermined distance from the surface of the specimen and operable for sensing the predetermined distance between the proximity detector sensor and the surface of the specimen; and providing a proximity detector actuator coupled to the substantially rigid base, the proximity detector actuator operable for maintaining the predetermined distance between the proximity detector sensor and the surface of the specimen as the substantially rigid base and the stylus are moved with respect to the surface of the specimen along the central axis of the stylus.

In summary, in a further exemplary embodiment, the present invention provides an apparatus for performing surface property measurements, such as workpiece hardness and other material property measurements, with in-process compensation for instrument frame distortion and the like, the apparatus including: a force loop around which a force is applied to a surface of a specimen; and a metrology loop around which a resultant interaction is measured, wherein the metrology loop is only partially coincident with the force loop. Preferably, the metrology loop is of a smaller relative size than the force loop.

Further areas of applicability of the present invention will be apparent to those of ordinary skill in the art from the detailed description and specific examples that follow. These exemplary embodiments are offered for purposes of illustration only, and are not intended to limit the scope of the present invention.

BRIEF DESCRIPTION OF THE DRAWINGS

The present invention is illustrated and described herein with reference to the various drawings, in which like reference numbers are used to denote like system components and/or method steps, as appropriate, and in which.

DETAILED DESCRIPTION OF THE INVENTION

Figure 1:
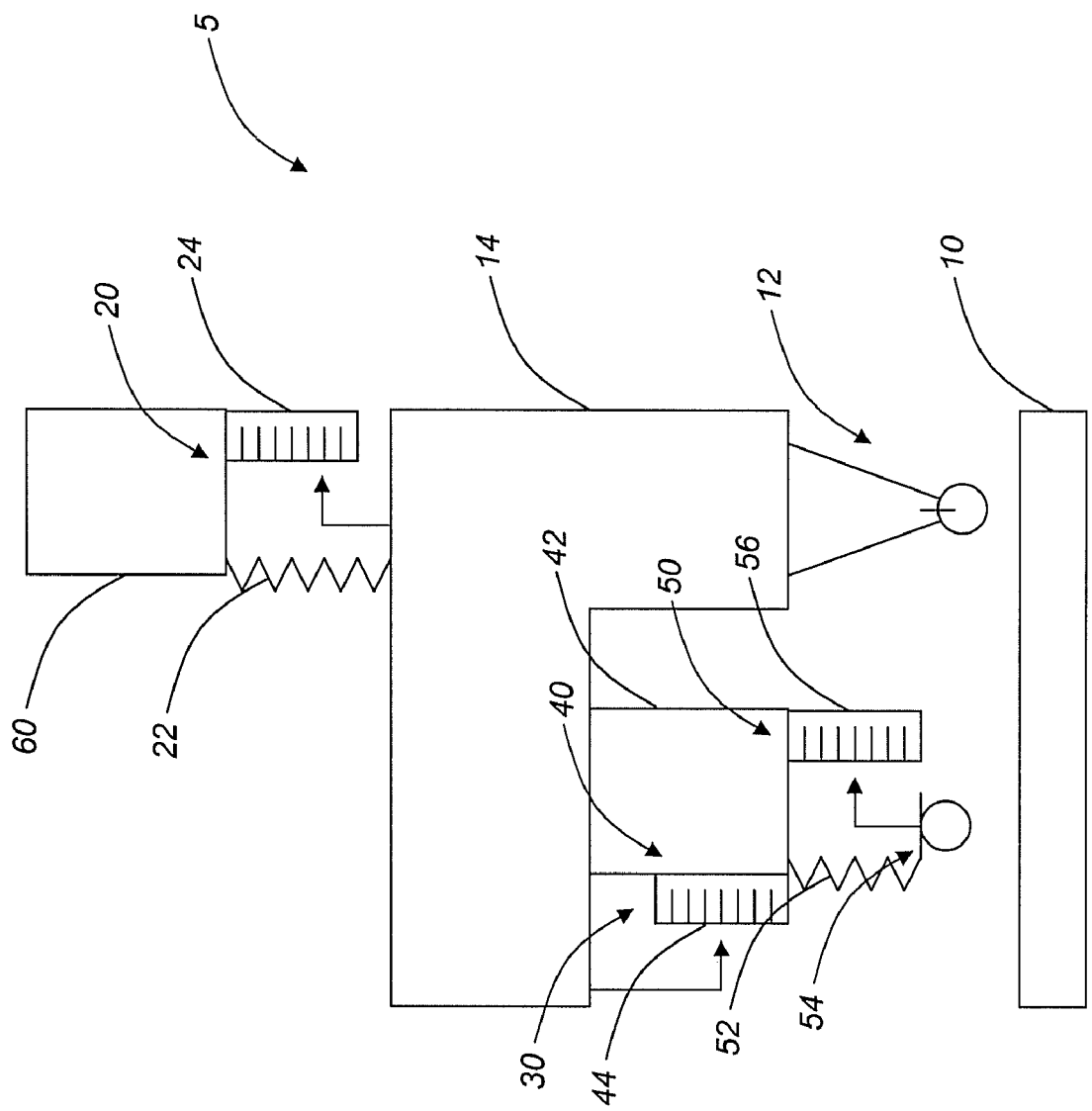
FIG. 1 is a schematic diagram illustrating one exemplary embodiment of the surface property measurement instrument of the present invention, operable for indenting and/or scratching the surface of a specimen.

Referring to FIG. 1, in one exemplary embodiment of the surface property measurement instrument 5 of the present invention, mechanical interaction occurs between a specimen 10 and an indenter stylus 12. The indenter stylus 12 may be, for example, a Berkovich 3-sided pyramid indenter stylus or the like. The indenter stylus 12 is attached to a relatively rigid base 14 that is in turn attached to a force measuring device 20 and a mechanism 30 for monitoring relative motion between the indenter stylus 12 and the specimen 10. The force measuring device 20 includes at least one load cell compliant support 22 and at least one load cell position sensor 24 for measuring relative motion between two points on the at least one load cell compliant support 22, typically between the two ends of the at least one load cell compliant support 22. This load cell 20 comprises, for example, a low-stiffness flexure mechanism having 4 linear leaf springs or the like. The mechanism 30 for monitoring relative motion between the indenter stylus 12 and the specimen 10 includes a servo mechanism 40 that is connected to the base 14 on one side and a proximity detector 50 on the other side. The servo mechanism 40 includes a proximity sensor actuator 42 operable for displacing the proximity detector 50 and at least one proximity detector positioning sensor 44 operable for measuring the displacement of the proximity sensor actuator 42. The proximity detector 50 includes at least one proximity detector compliant support 52 disposed between the proximity sensor actuator 42 and a proximity detector stylus 54, at least one proximity detector position sensor 56 operable for converting to a voltage the proximity between the proximity detector stylus 54 and the surface of the specimen 10. This reference sensor 30 comprises, for example, an atomic force microscopy (AFM) probe or the like, for which calibration is not necessary, as a constant signal (displacement) need only be maintained using a piezoelectric transducer (PZT) servo or the like. All of these components are attached to a base actuator 60 that is used to drive the indenter stylus 12 into contact with the surface of the specimen 10.

In operation, the surface property measurement instrument 5 is used to indent the surface of the specimen 10. Prior to any measurement, it is assumed that the indenter stylus is clear of the surface of the specimen 10. The surface property measurement instrument is then translated towards the surface of the specimen using the base actuator 60. Before the indenter stylus 12 contacts the surface of the specimen 10, the proximity detector stylus 54 is extended using the proximity sensor actuator 42. Preferably, the proximity detector stylus 54 is extended to be nearer the surface of the specimen 10 than the indenter stylus 12. Thus, as the base actuator 60 brings the surface property measurement instrument 5 towards the surface of the specimen 5, the at least one proximity detector position sensor 56 is first to produce a change in signal. With continuing motion towards the surface of the specimen 10, there is a resulting change in the signal associated with the at least one proximity detector position sensor 56. Before the indenter stylus 12 makes contact with the surface of the specimen 10, and at a given signal value associated with the at least one proximity detector position sensor 56, the proximity sensor actuator 42 acts to maintain this signal value associated with the at least one proximity detector position sensor 56. Importantly, the proximity detector stylus 54 is held at a constant position relative to and in a constant interaction with the surface of the specimen 10 during measurement. As the base actuator 60 continues to drive the surface property measurement instrument 5 towards the surface of the specimen 10, the indenter stylus 12 approaches and eventually contacts the surface of the specimen 10, resulting in interaction forces between these two bodies. Interaction forces occur both prior to and after physical contact. Changes in interaction forces between the indenter stylus 12 and the surface of the specimen 10 induce a displacement in the at least one load cell compliant support of the force measuring device 20, which is measured by the at least one load cell position sensor 24. Because there are no other varying forces associated with the mechanism, which is suitably calibrated, the force measuring device 20 monitors only changes in interaction force between the indenter stylus 12 and the surface of the specimen 10. Thus, the goals of the present invention are achieved.

Figure 2:
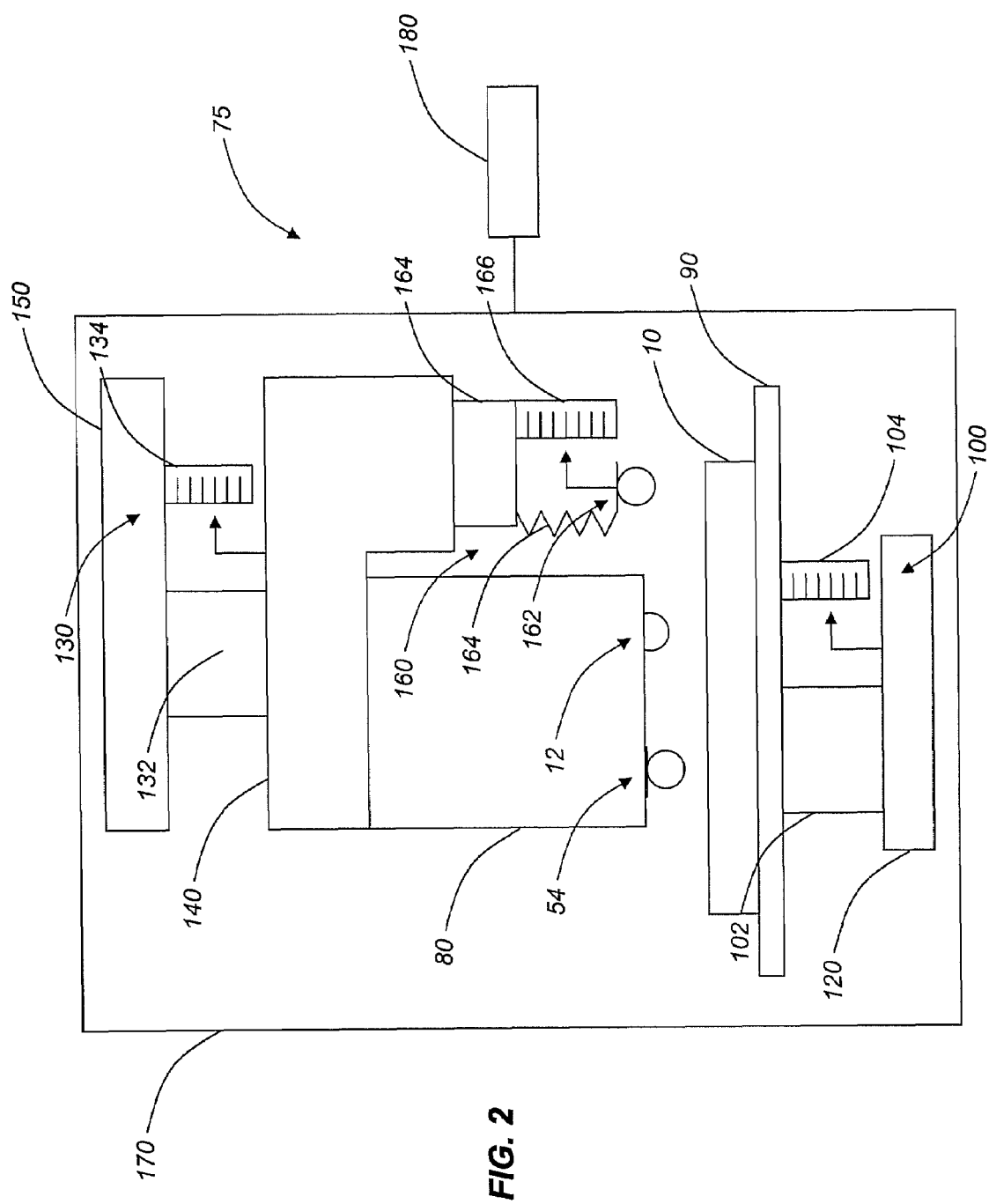
FIG. 2 is a schematic diagram illustrating another exemplary embodiment of the surface property measurement instrument of the present invention, operable for indenting and/or scratching the surface of a specimen, translating and/or rotating the apparatus with respect to the specimen, and scanning the surface of the specimen under controlled conditions.

Referring to FIG. 2, in another exemplary embodiment of the surface property measurement instrument 75 of the present invention, the surface property measurement instrument 75 includes a gage cover 80 from which the indenter stylus 12 and proximity detector stylus 54 protrude. Optionally, the gage cover 80 includes insulative shielding operable for reducing environmental effects on the surface property measurement instrument 75.

The above-referenced functionality is maintained and additional systems are employed to characterize additional material properties and/or observe additional material phenomena. The specimen 10 is secured to a relatively rigid specimen platform 90. A specimen positioning system 100 is used to position the specimen 10 and may be utilized in a scanning mode. The specimen positioning system 100 includes at least one specimen positioning system actuator 102 operable for positioning the specimen platform 90 with respect to the instrument frame 120 and at least one specimen positioning system sensor 104 operable for measuring the displacement of the at least one specimen positioning system actuator 102. The purpose of the specimen positioning system 100 is to create arrays of indentations or scratches for topographic scanning, for example. The specimen positioning system 100 has the ability to move the specimen platform 90 in at least one coordinate direction.

The translation stage 130 includes at least one translation stage actuator 132 operable for positioning the relatively rigid platform 140 with respect to the instrument frame 150 and at least one translation stage sensor 134 operable for measuring the displacement of the at least one translation stage actuator 132. Thus, the major components of this embodiment attach to the instrument frame 120, 150 at two or more points, for example. It is assumed that these points are part of the same instrument frame. Due to the attributes of the present invention, this instrument frame has only a minimal influence on the function of the surface property measurement instrument 75.

Of particular relevance to the measurement of surface properties, in some applications, is the integration of a scanned probe microscope (SPM) or the like. Optionally, a scanned probe microscope system 160 is attached to the platform 140. The scanned probe microscope system 160 includes at least one probe operable for obtaining localized surface property measurements utilizing a stylus profilometry and/or scanned probe microscopy methodology, both of which are known to those of ordinary skill in the art. The scanned probe microscopy methodology employs an SPM "tip" 162 that is attached to an SPM actuator 134 via at least one SPM spring 134 or other support. The interaction between the SPM "tip" 162 and the surface of the specimen 10 is measured using at least one SPM sensor 166. The motion of the SPM actuator 164 in all coordinates is measured by the at least one SPM sensor 166. The surface of the specimen 10 is measured by bringing the SPM "tip" 162 close to the surface of the specimen 10, such that there is a measurable signal in the at least one SPM sensor 166. Typically, the at least one probe is scanned over the surface of the specimen 10 while the interaction of the SPM "tip" 162 is maintained at a constant signal value by moving the SPM "tip" 162 normal to the surface of the specimen 10 using the SPM actuator 134. A map of this surface interaction is thereby generated.

Optionally, the surface property measurement instrument 75 is housed in an environmental control chamber 170, wherein properties such as temperature, pressure, and humidity may be continuously monitored and controlled by a data acquisition (DAQ) system 180. This DAQ system 180 has the ability to continuously monitor all sensors present, with or without feedback, and control all actuators present.

Figure 3:
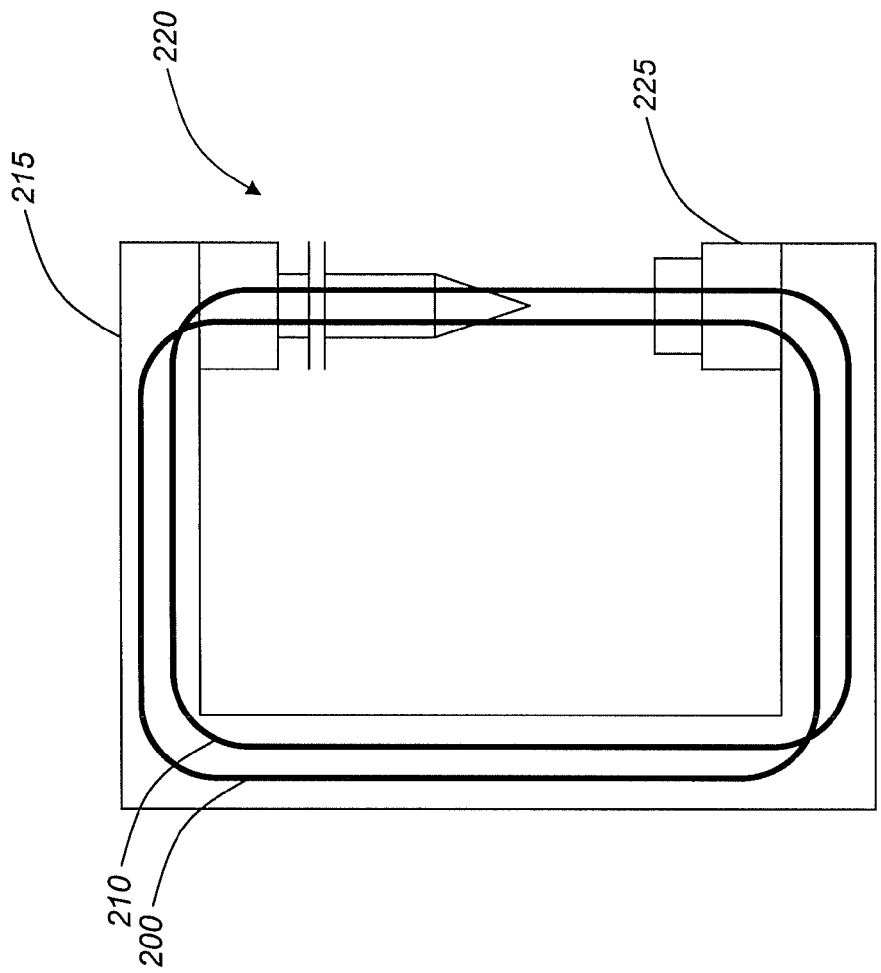
FIG. 3 is a schematic diagram illustrating the coincident force loop(s) and metrology loop(s) associated with a conventional surface property measurement instrument.

Referring to FIG. 3, the force loop(s) 200 and metrology loop(s) 210 associated with a conventional surface property measurement instrument 220 are largely coincident. Thus, such an instrument 220 is effectively measuring both the depth of the indentation created, as well as the displacement of the frame 215 and stage 225. This is problematic as the typical compliance required is less than about 10 nm per mN. As is well known to those of ordinary skill in the art, perfect indenter styli are impossible to manufacture. Tip blunting and non-singular tips are common. Improper orientation of the central axis may cause significant errors. Thus, the surface property measurement instrument of the present invention is advantageous as it automatically minimizes and compensates for these imperfections.

Figure 4:
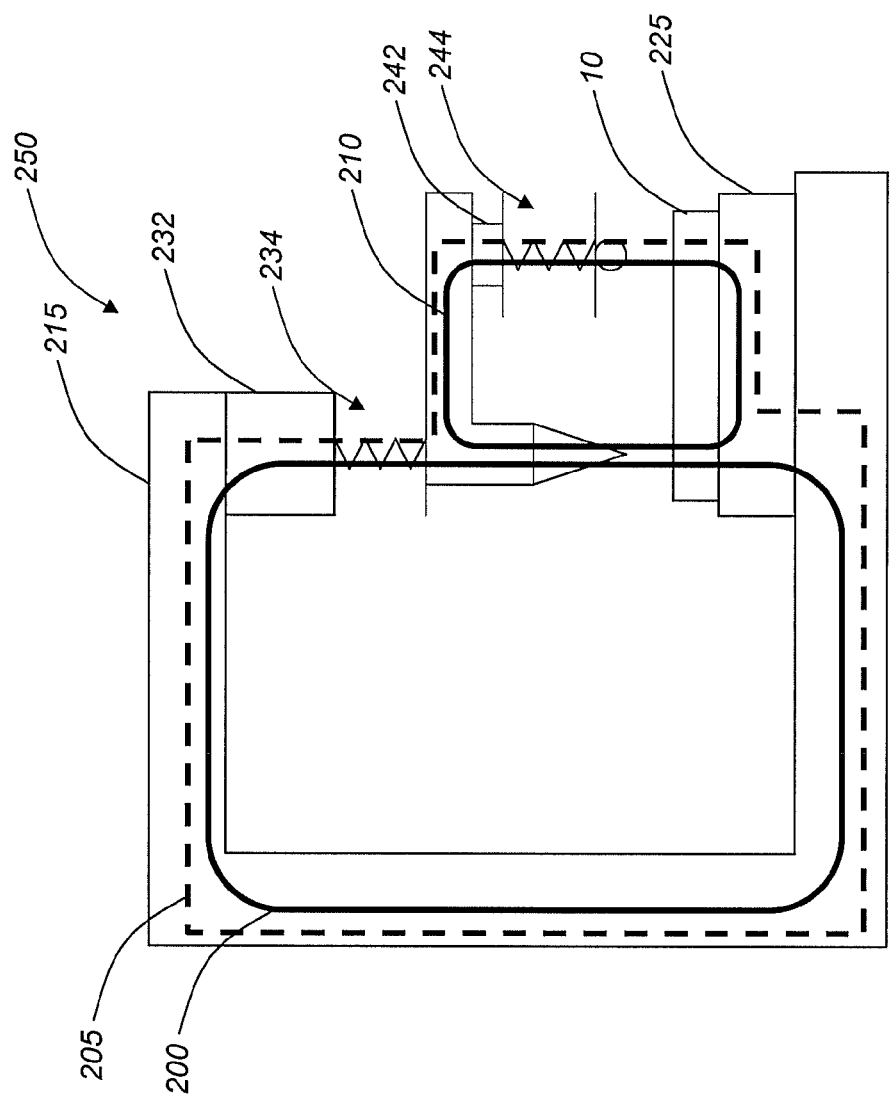
FIG. 4 is a schematic diagram illustrating the separate force loop(s) and metrology loop(s) associated with the surface property measurement instrument of the present invention.

Referring to FIG. 4, the force loop(s) 200 and metrology loop(s) 210 associated with the above-referenced embodiments of the surface property measurement instrument 250 of the present invention are largely separate, with the metrology loop(s) 210 being substantially shorter in length. In addition to the motion actuator 232 and load cell 234, the reference sensor 244 also partially defines a secondary force loop 205. The servo actuator 242 maintains a constant distance between the surface of the specimen 10 and the reference sensor 244. Thus, deflections of the frame 215 and stage 225 are directly measured and effectively removed from the equation.

Is should be noted that, in the above-referenced embodiments, any and all contact-based sensors utilized may include contact-based resonant probes or distortion-based flexure probes that measure distortion under an applied load using capacitance sensors, inductance sensors, strain gages, optical sensors, piezoelectric sensors, piezoresistive sensors, linear variable differential transformers (LVDTs), and/or ultrasonic sensors, or the like. Any and all non-contact-based sensors utilized may include capacitance sensors, interferometers, optical interferometers, ultrasonic probes, tunneling probes, and/or resonant probes, or the like—any and all of which sense near-contact phenomena, such as air squeeze films, eddy currents, magnetic waves, gas pressures, liquid pressures, and/or electrostatic charges, or the like.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. An apparatus for performing surface property measurements with in-process compensation for instrument frame distortion and the like, the apparatus comprising:
    a substantially rigid base;
    a stylus coupled to the substantially rigid base, the stylus configured and selectively positioned to interact with a surface of a specimen at points generally along a central axis of the stylus;
    a proximity detector sensor coupled to the substantially rigid base, the proximity detector sensor disposed at a predetermined constant distance from the surface of the specimen and operable for sensing the predetermined constant distance between the proximity detector sensor and the surface of the specimen, wherein the proximity detector sensor is movable relative to the stylus;
    a proximity detector actuator coupled to the substantially rigid base, the proximity detector actuator operable for maintaining the predetermined constant distance between the proximity detector sensor and the surface of the specimen as the substantially rigid base and the stylus are moved with respect to the surface of the specimen along the central axis of the stylus; and
    a proximity detector translation sensor coupled to the substantially rigid base, the proximity detector translation sensor operable for sensing a displacement of the proximity detector sensor relative to the substantially rigid base while the stylus is interacting with the surface of the specimen.

2. The apparatus of claim 1, wherein sensing the displacement of the proximity detector sensor relative to the substantially rigid base while the stylus is interacting with the surface of the specimen comprises measuring the relative motion of the proximity detector actuator.

3. The apparatus of claim 2, wherein the displacement of the proximity detector sensor relative to the substantially rigid base while the stylus is interacting with the surface of the specimen represents a degree of interaction of the stylus with the surface of the specimen.

4. The apparatus of claim 3, wherein the displacement of the proximity detector sensor relative to the substantially rigid base while the stylus is interacting with the surface of the specimen represents the degree of interaction of the stylus with the surface of the specimen free from influence of a displacement of one or more of a frame, a stage, and a load cell, each forming a portion of the apparatus.

5. The apparatus of claim 1, further comprising a translation sensor and a translation actuator operable for positioning the specimen in a direction normal to the central axis of the stylus.

6. The apparatus of claim 1, further comprising a scanned probe microscope system comprising at least one probe operable for obtaining a localized surface property measurement, the at least one probe utilizing one or more of a stylus profilometry methodology and a scanned probe microscopy methodology.

7. The apparatus of claim 1, further comprising an environmental control chamber operable for monitoring and controlling one or more of temperature, pressure, and humidity around the apparatus.

8. The apparatus of claim 1, further comprising a data acquisition system operable for monitoring one or more of any sensors forming a portion of the apparatus.

9. The apparatus of claim 1, further comprising a control system operable for controlling one or more of any actuators forming a portion of the apparatus.

10. The apparatus of claim 1, wherein the interaction with the surface of the specimen is one or more of a contact-based interaction and a non-contact-based interaction.

11. The apparatus of claim 1, further comprising a load cell sensor coupled to the substantially rigid base, the load cell sensor operable for sensing an interaction force between components contacting the surface of the specimen.

12. A method for performing surface property measurements with in-process compensation for instrument frame distortion and the like, the method comprising:
   providing a substantially rigid base;
   providing a stylus coupled to the substantially rigid base, the stylus configured and selectively positioned to interact with a surface of a specimen at points generally along a central axis of the stylus;
   providing a proximity detector sensor coupled to the substantially rigid base, the proximity detector sensor disposed at a predetermined constant distance from the surface of the specimen and operable for sensing the predetermined constant distance between the proximity detector sensor and the surface of the specimen, wherein the proximity detector sensor is movable relative to the stylus;
   providing a proximity detector actuator coupled to the substantially rigid base, the proximity detector actuator operable for maintaining the predetermined constant distance between the proximity detector sensor and the surface of the specimen as the substantially rigid base and the stylus are moved with respect to the surface of the specimen along the central axis of the stylus; and
   providing a proximity detector translation sensor coupled to the substantially rigid base, the proximity detector translation sensor operable for sensing a displacement of the proximity detector sensor relative to the substantially rigid base while the stylus is interacting with the surface of the specimen.

13. The method of claim 12, wherein sensing the displacement of the proximity detector sensor relative to the substantially rigid base while the stylus is interacting with the surface of the specimen comprises measuring the relative motion of the proximity detector actuator.

14. The method of claim 13, wherein the displacement of the proximity detector sensor relative to the substantially rigid base while the stylus is interacting with the surface of the specimen represents a degree of interaction of the stylus with the surface of the specimen.

15. The method of claim 14, wherein the displacement of the proximity detector sensor relative to the substantially rigid base while the stylus is interacting with the surface of the specimen represents the degree of interaction of the stylus with the surface of the specimen free from influence of a displacement of one or more of a frame, a stage, and a load cell, each forming a portion of the apparatus.

16. The method of claim 12, further comprising providing a translation sensor and a translation actuator operable for positioning the specimen in a direction normal to the central axis of the stylus.

17. The method of claim 12, further comprising providing a scanned probe microscope system comprising at least one probe operable for obtaining a localized surface property measurement, the at least one probe utilizing one or more of a stylus profilometry methodology and a scanned probe microscopy methodology.

18. The method of claim 12, further comprising providing an environmental control chamber operable for monitoring and controlling one or more of temperature, pressure, and humidity around the apparatus.

19. The method of claim 12, further comprising providing a data acquisition system operable for monitoring one or more of any sensors forming a portion of the apparatus.

20. The method of claim 12, further comprising providing a control system operable for controlling one or more of any actuators forming a portion of the apparatus.

21. The method of claim 12, wherein the interaction with the surface of the specimen is one or more of a contact-based interaction and a non-contact-based interaction.

22. The method of claim 12, further comprising providing a load cell sensor coupled to the substantially rigid base, the load cell sensor operable for sensing an interaction force between components contacting the surface of the specimen.

23. An apparatus for performing surface property measurements with in-process compensation for instrument frame distortion and the like, the apparatus comprising:
   a force loop around which a force is applied to a surface of a specimen; and
   a metrology loop around which a resultant interaction is measured, wherein the metrology loop is only partially coincident with the force loop;
   wherein the metrology loop comprises:
   a proximity detector sensor disposed at a predetermined constant distance from the surface of the specimen and operable for sensing the predetermined constant distance between the proximity detector sensor and the surface of the specimen, wherein the proximity detector sensor is movable relative to a stylus; and
   a proximity detector actuator operable for maintaining the predetermined constant distance between the proximity detector sensor and the surface of the specimen.

24. The apparatus of claim 23, wherein the metrology loop is of a smaller relative size than the force loop.

* * * * *